(12) United States Patent
Kuo

(10) Patent No.: US 8,096,936 B2
(45) Date of Patent: Jan. 17, 2012

(54) THERMOTHERAPY DEVICE WITH AN INFLATABLE HOOD

(75) Inventor: Arthur Kuo, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 890 days.

(21) Appl. No.: 12/136,265

(22) Filed: Jun. 10, 2008

(65) Prior Publication Data
US 2008/0319249 A1 Dec. 25, 2008

(30) Foreign Application Priority Data
Jun. 19, 2007 (DE) .......... 10 2007 028 128

(51) Int. Cl.
*A61G 11/00* (2006.01)
(52) U.S. Cl. ...................................... 600/22
(58) Field of Classification Search .............. 600/21, 600/22; 128/205.26, 201.23, 201.25, 202.12, 128/202.18, 204.16; 312/1, 3; 5/97; 454/187
See application file for complete search history.

(56) References Cited

U.S. PATENT DOCUMENTS

| 3,818,896 A | * | 6/1974 | Deaton | 600/22 |
| 5,230,611 A | * | 7/1993 | Shelton | 417/437 |
| 5,817,002 A | | 10/1998 | Donnelly et al. | |
| 5,832,919 A | * | 11/1998 | Kano et al. | 128/205.26 |
| 6,217,507 B1 | * | 4/2001 | Bonvik | 600/21 |

FOREIGN PATENT DOCUMENTS

| WO | WO 97 43995 A1 | 11/1997 |
| WO | WO 99 48426 A1 | 9/1999 |

* cited by examiner

*Primary Examiner* — Samuel Gilbert
(74) *Attorney, Agent, or Firm* — McGlew and Tuttle, P.C.

(57) ABSTRACT

A thermotherapy device with a reclining surface and with an inflatable hood for covering the reclining surface. The inflatable hood (1) is provided with a plurality of inflatable, tubular support elements (3) with plastic films (2) arranged between them, which tenter one or more surfaces between the support elements (3) in the inflated state.

20 Claims, 4 Drawing Sheets

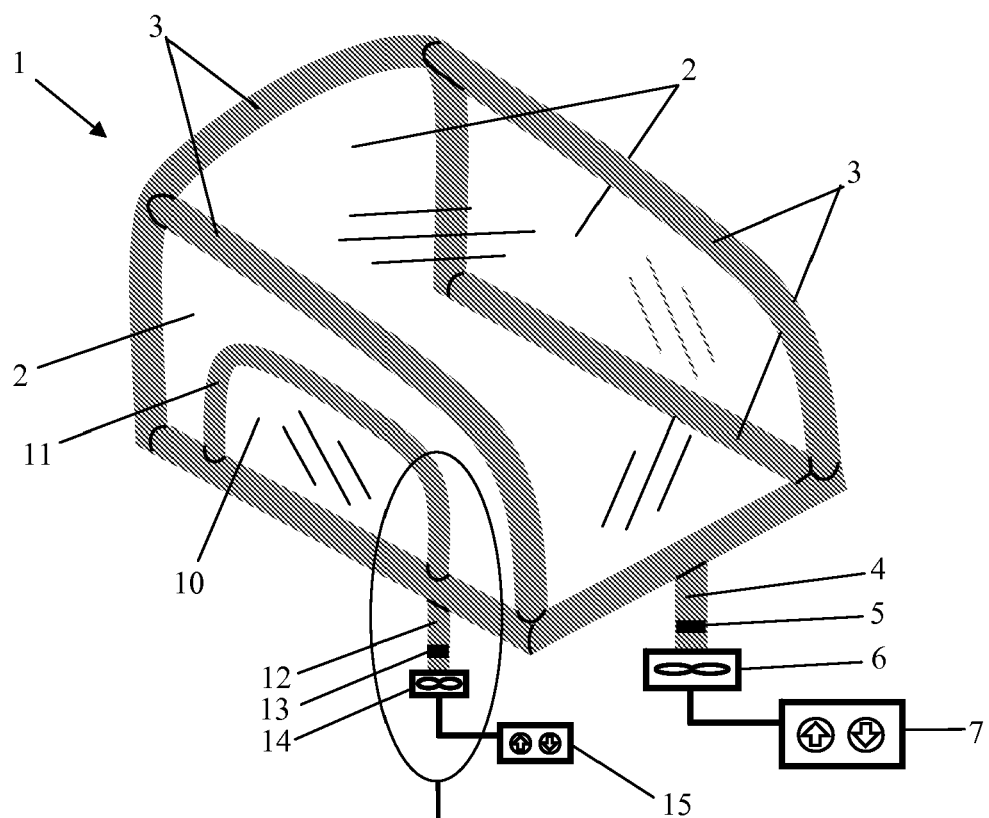
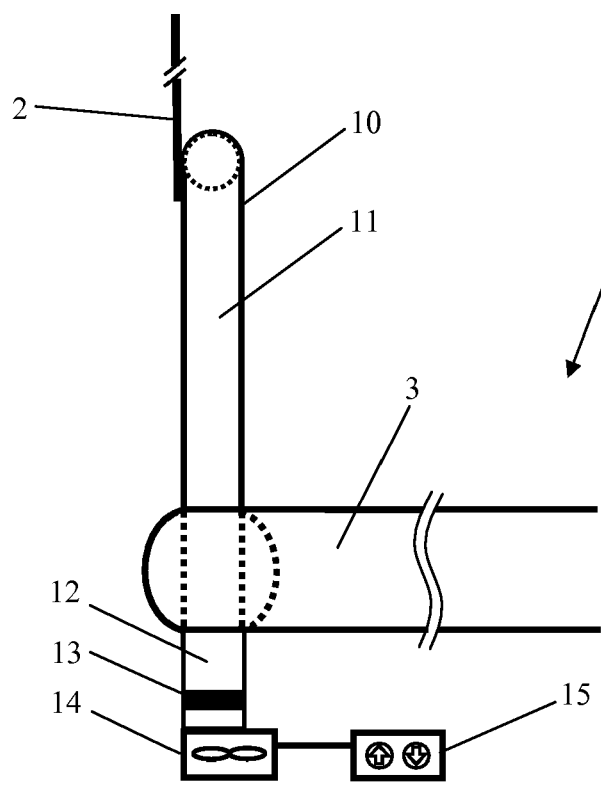
Fig. 4A
Fig. 4B

THERMOTHERAPY DEVICE WITH AN INFLATABLE HOOD

CROSS REFERENCE TO RELATED APPLICATIONS

This application claims the benefit of priority under 35 U.S.C. §119 of German Patent Application DE 10 2007 028 128.7 filed Jun. 19, 2007, the entire contents of which are incorporated herein by reference.

FIELD OF THE INVENTION

The present invention pertains to a thermotherapy device with a reclining surface and with an inflatable hood for covering the reclining surface.

BACKGROUND OF THE INVENTION

The thermal balance is maintained for premature and newborn patients who are under medical care at present essentially either by incubators which are well conditioned and closed by means of a hood or by open care beds, into which, in general, infrared radiation is sent, and in which good accessibility for the treatment is associated with an undesirably high skin temperature and with a great loss of water due to evaporation. An essential drawback of the prior-art incubators is the limited accessibility for medical treatment and care. It is therefore desirable to combine the positive properties of the two prior-art types of devices in a new device. Such so-called hybrid thermotherapy devices combine design features of both the open care beds and of the closed incubators. For example, U.S. Pat. No. 5,817,002 proposes a thermotherapy device, which can be switched over between a closed incubator and an open care bed, the hood being able to be divided and folded up when needed.

One drawback of this design is that much time and space are required for displacing the hood and the side walls and that the construction and control are complicated.

SUMMARY OF THE INVENTION

The object of the present invention is to provide a hybrid thermotherapy device, which is substantially improved in terms of handling.

According to the invention, a thermotherapy device is provided comprising a reclining surface and an inflatable hood for covering the reclining surface. The inflatable hood comprises a plurality of inflatable tubular support elements and plastic film elements between the tubular support elements to form one or more surfaces between the tubular support elements in an inflated state.

The thermotherapy device according to the invention makes possible the problem-free handling of the thermotherapy device for the care of a patient on the reclining surface due to the design embodiment of the hood, which can be placed or deposited on the reclining surface when needed and consists of a lightweight construction with inflatable support elements with plastic films between the support elements, which plastic films are arranged in between and are tentered by the support elements.

Advantageously one or more of the plastic film elements are directly above the reclining surface and/or on sides of the reclining surface. The support elements may be connected to one another such that the support elements have none of the plastic film elements in an area of one of the shorter sides of the reclining surface in the inflated state, so that the one of shorter sides is open.

A wall with a canopy portion may be provided for sealing and/or stabilizing a mounting of the hood on one of the shorter sides of the reclining surface.

The plastic film may consist of a plastic that is one of transparent and transparent to infrared radiation. The plastic film may consist of a plastic including polypropylene.

At least one of the support elements may have a removable nonreturn valve for taking in air into the one of the support elements or into all or a plurality of the support elements.

At least one of the support elements may include a resetting element comprising an elastic cord.

At least one of the support elements may be provided with openings, perforations or pores for releasing conditioned air from an interior of the at least one of the support elements into an interior space defined by the hood and the reclining surface.

The inflatable hood may further comprise a separate side window with an inflatable window support element. A window support element may advantageously be integrated in the inflatable hood.

At least one of the plastic film elements may advantageously have a double-walled design.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 4A is a perspective schematic view showing an inflated and raised hood with an openable side window;

FIG. 4B is a schematic detail view of the side window;

DESCRIPTION OF THE PREFERRED EMBODIMENTS

Figure 1:
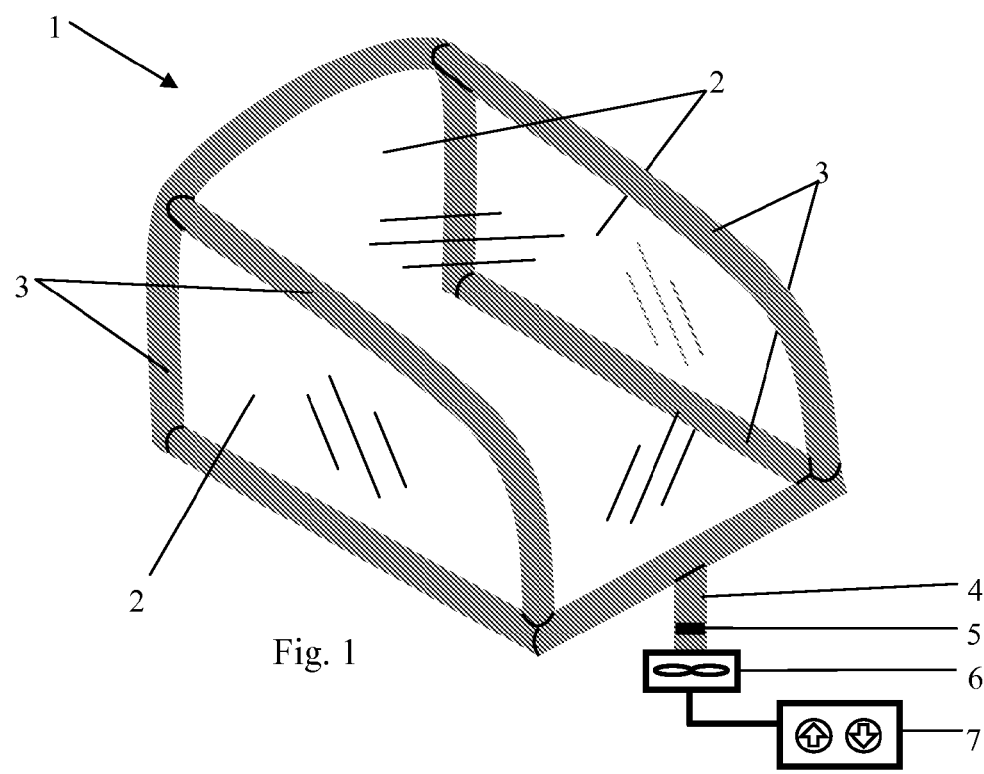
FIG. 1 is a perspective schematic view of an inflated and raised hood of a thermotherapy device.

Referring to the drawings in particular, the thermotherapy devices according to the invention, which can be used as hybrid thermotherapy devices, have no solid and difficult-to-handle hoods and side walls made of plexiglass, which must be folded sideways or downward, sunk or displaced for opening.

The hood 1, which in the inflated or pumped-up and hence raised state in FIG. 1, has a plurality of support elements 3, which are connected to one another in the form of a frame and which tenter (stretch), on, e.g., three sides, a plastic film 2 each between the support elements 3 such that the reclining surface can be covered with the hood 1, which can be placed on the reclining surface of the thermotherapy device.

Elastic, thin plastic films 2 made of polypropylene, which are permeable to infrared radiation and x-rays, are preferably used to build up the hood 1 with an upper wall and two side walls. The plastic films 2 have a thickness of, e.g., approximately 0.2 mm to 0.4 mm, depending on the intended use. The hood 1 has dimensions corresponding to those in a prior-art incubator, i.e., for example, a length of 700 mm, a width of 500 mm and a height of 40 mm. The inflatable tubular support elements 3 consisting of a film or a plastic laminate with a diameter of about 25 mm are connected to one another and have a support element interface 4 with a built-in, quickly removable nonreturn valve 5 to a fan 6 on the foot side. A control unit 7 controls the nonreturn valve 5 and the fan 6 in order to pump air into the support elements 3 and to remove the nonreturn valve 5 as needed when the air shall be let out from the support elements.

Figure 2:
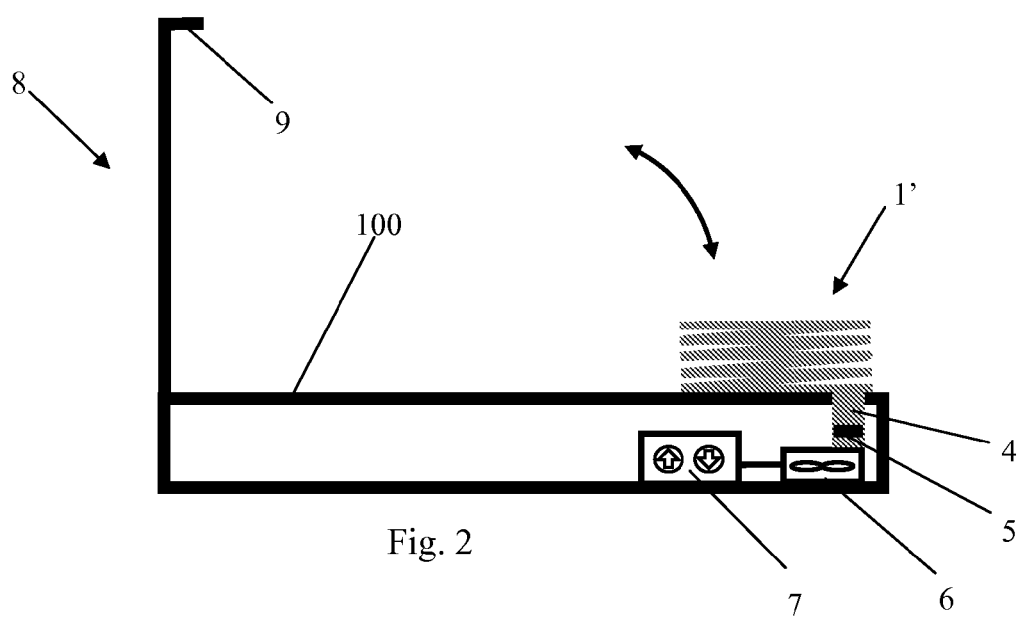
FIG. 2 is a side schematic view of a thermotherapy device with a hood in the non-inflated state.
Figure 3:
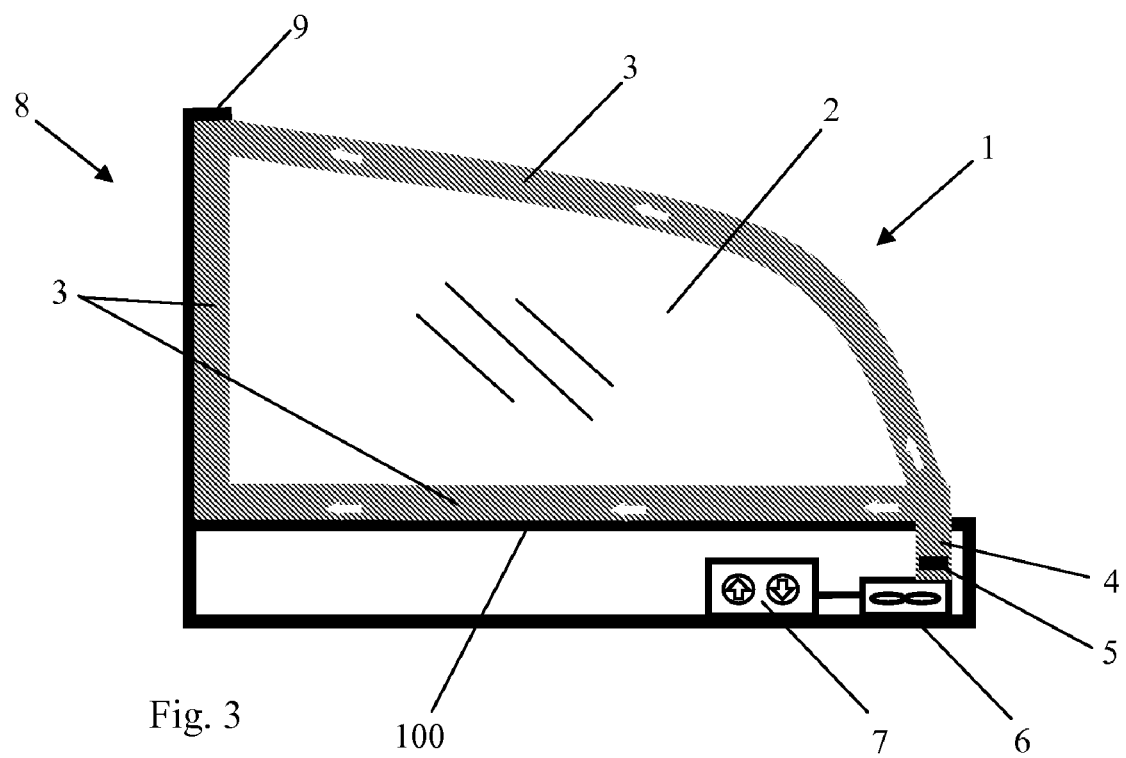
FIG. 3 is a side schematic view of the thermotherapy device according to FIG. 2 with the hood inflated and raised.

The hood 1 in FIG. 1 or the hood 1' in FIG. 2 is folded or rolled before it is put into operation for the first time and is packed in a package in a sterile form. After unpacking, the folded hood 1' according to FIG. 2 is connected to the thermotherapy device 8, which is shown schematically in FIG. 2, and is connected to the fan 6 via the support element interface 4. By pumping in the air, the hood 1, 1' expands, and the support elements 3 filled with air act as frame or support structure elements, which tenter the plastic films 2 between them, see FIGS. 1 and 3.

The nonreturn valve 5 ensures a slight overpressure in the support elements 3 in the pumped-up state of the hood 1. The hood 1 can be uncoupled from the support element interface 4 and hence from the fan 6 when needed.

To improve the pneumatic sealing and the stabilizing mounting between the hood 1 and the thermotherapy device 8, a closing wall especially with a short canopy 9 is optionally arranged on the head side of the thermotherapy device 8, so that the hood 1 is pushed in the direction of the reclining surface 100 and stabilized. After the air has been let out in the support elements 3, the hood 1 collapses again, so that the hood 1 can be separated from the fan 6 via the support element interface 4 and optionally removed from the reclining surface 100.

FIG. 4A shows a design of the hood 1 for the thermotherapy device 8 with additional side windows 10, which has a window support element 11 with a diameter of, e.g., 15 mm. FIG. 4B shows a detail when viewed from the foot side. The plastic film 2 between the lateral support elements 3 of this side is correspondingly open. The window support element 11 is structurally integrated in a lower support element 3 of the hood 1, but it has an air guide of its own. For example, the side window 10 has a length of 500 mm and a height of 25 mm. The side window 10 is controlled by a separate second fan 14 and a second control unit 15 via the window support element interface 12 and the second nonreturn valve 13.

If air is pumped by the second fan 14 into the window support element 11, the latter stands up, tenters the plastic film 2 of the side window 10 therebetween and thus closes the side window 10.

When the air is let out or drawn off, the window support elements 11 collapse after removal of the second nonreturn valve 13 and the side window 10 opens.

The window support element 11 of the side window 10 is designed such that it is slightly oblique towards the outside, so that the side window 10 slopes outwardly in the tentered, raised state and presses the plastic film 2 for improved sealing.

One side window 10 each may also be arranged on both long sides of the thermotherapy device 8.

Figure 5:
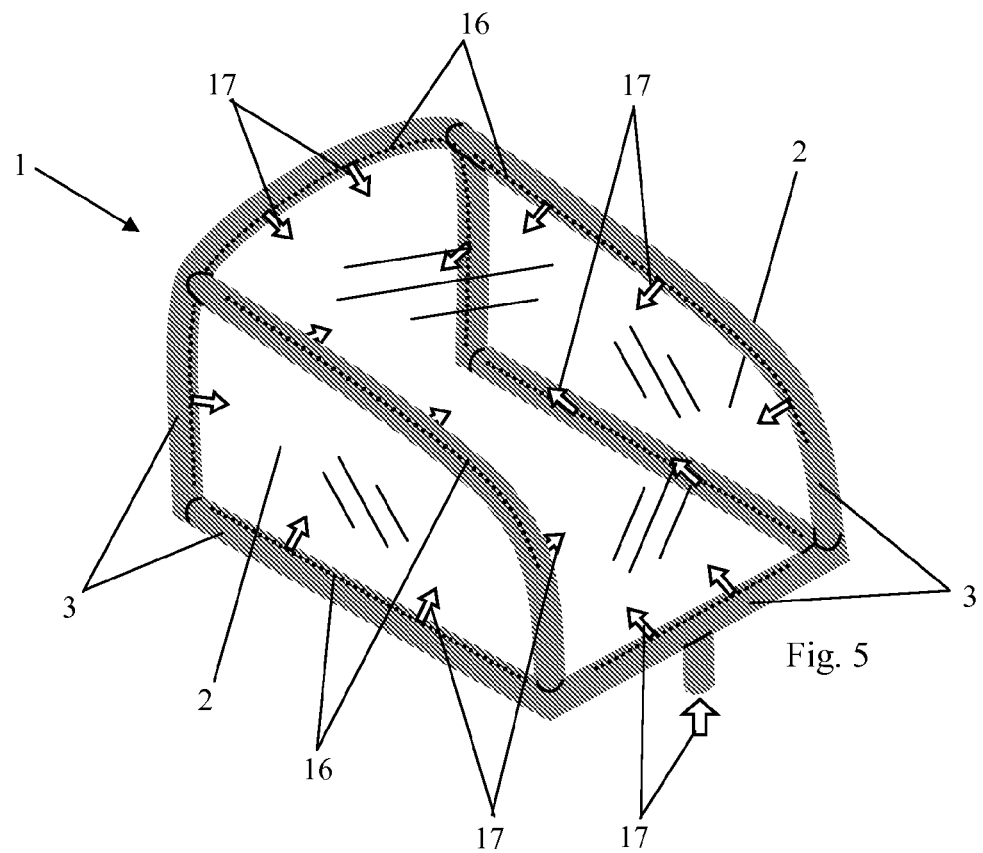
FIG. 5 is a perspective schematic view showing an inflated and raised hood with openings in the support element.

If the support elements 3 are connected directly to the supply unit for conditioned warm and humid air of the thermotherapy device 8 according to FIG. 5, the support elements 3 are preferably provided especially with small perforations or pores 16 in the direction of the interior space of the hood 1. As a result, the conditioned and humidified air flow 17 is sent directly into the interior space in which the patient is accommodated.

Figure 6:
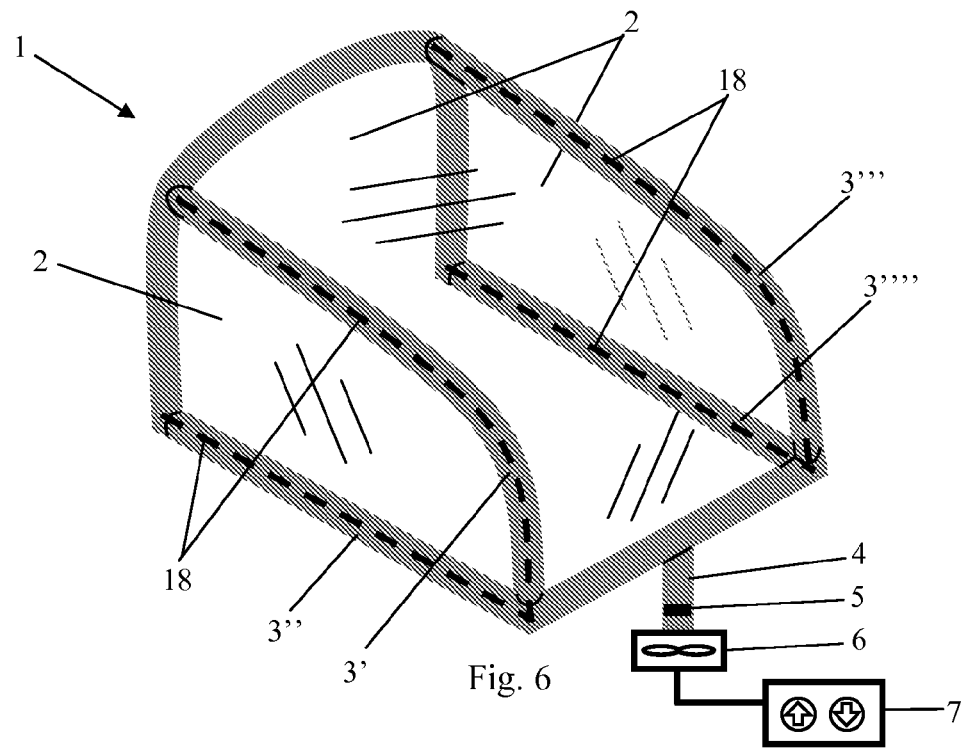
FIG. 6 is a perspective schematic view of an embodiment of a hood with resetting elements in the support elements.

In the embodiment according to FIG. 6, the support elements 3', 3'', 3''', 3'''' are provided with resetting elements 18, schematically represented as linear elements, so that the hood 1 contracts and folds up and the air is let out or drawn off in the direction of the foot side, i.e., towards the right lower corner in the figure. The resetting elements 18 are, for example, elastic cords made of rubber with a diameter of a few mm, a maximum stretchability in the longitudinal direction of, for example, 700%, and a low tensile strength of about 250 g at 400% elongation.

The resetting elements 18 are preferably fastened to the respective ends of the elongated support elements 3', 3'', 3''', 3'''' at the time of manufacture of the hood 1. The resetting elements 18 exert no resetting force on the hood 1 in the folded-up state of the hood 1.

The hood 1 may also be designed as a double-walled hood in all embodiments in order to avoid loss of heat through the plastic film 2.

The hood 1 may also be a disposable hood.

For a simple embodiment, the hood 1 is inflated by means of a sealable inflating opening.

While specific embodiments of the invention have been shown and described in detail to illustrate the application of the principles of the invention, it will be understood that the invention may be embodied otherwise without departing from such principles.

What is claimed is:

1. A thermotherapy device comprising:
a reclining surface;
an inflatable hood for covering the reclining surface, said inflatable hood comprising a plurality of inflatable tubular support elements and plastic film elements between said tubular support elements to form one or more surfaces between said tubular support elements in an inflated hood state, wherein at least one of said support elements is provided with openings, perforations or pores and defines a conditioned warm and humid air conduit for conveying and for releasing gas from an interior of at least one of said support elements into an interior space defined by said hood and said reclining surface;
an inflation means connected to said inflatable tubular support elements for inflating said inflatable tubular support elements, said support elements supporting said plastic film elements in said inflated hood state in a region around said reclining surface to provide a deployed hood state; and
a supply unit for supplying conditioned warm and humid air, said supply unit being connected to said at least one of said support elements provided with openings via said inflation means to provide a conditioned warm and humid air flow to said at least one of said support elements provided with openings and send conditioned warm and humid air directly into said interior space in said inflated hood state.

2. A thermotherapy device in accordance with claim 1, wherein said support elements are connected to one another such that said plastic film elements are tentered between said support elements including one or more plastic film elements directly above said reclining surface or on sides of said reclining surface.

3. A thermotherapy device in accordance with claim 1, wherein said support elements are connected to one another such that said support elements have none of said plastic film elements in an area of one of shorter sides of said reclining surface in the inflated state, so that said one of shorter sides is open.

4. A thermotherapy device in accordance with claim 3, further comprising a wall with a canopy portion, said wall for sealing and/or stabilizing a mounting of said hood on one of the shorter sides of the reclining surface.

5. A thermotherapy device in accordance with claim 1, wherein said plastic film consists of a plastic that is one of transparent and transparent to infrared radiation, wherein said plastic film includes polypropylene.

6. A thermotherapy device in accordance with claim 1, wherein at least one of said support elements has a removable nonreturn valve for taking in air into said one of said support elements or into all or a plurality of said support elements.

7. A thermotherapy device in accordance with claim 1, wherein said inflatable hood further comprises a separate side window with an inflatable window support element, said inflatable window support element being integrated in said inflatable hood.

8. A thermotherapy device in accordance with claim 1, wherein at least one of said plastic film elements has a double-walled design.

9. A thermotherapy device comprising:
a reclining surface; and
an inflatable hood for covering the reclining surface, said inflatable hood comprising a plurality of inflatable tubular support elements and plastic film elements between said tubular support elements to form one or more surfaces between said tubular support elements in an inflated state, wherein at least one of said support elements includes a resetting element comprising an elastic cord.

10. A thermotherapy device comprising:
a reclining surface; and
an inflatable hood for covering the reclining surface, said inflatable hood comprising a plurality of inflatable tubular support elements and plastic film elements between said tubular support elements to form one or more surfaces between said tubular support elements in an inflated state, wherein said support elements are connected to one another such that said support elements have none of said plastic film elements in an area of one of shorter sides of said reclining surface in the inflated state, so that said one of shorter sides is open; and
a wall with a canopy portion, said wall for sealing and/or stabilizing a mounting of said hood on one of the shorter sides of the reclining surface.

11. A thermotherapy device comprising:
a reclining surface;
an inflatable hood for covering the reclining surface, said inflatable hood comprising a plurality of inflatable tubular support elements and plastic film elements between said tubular support elements;
an inflation means connected to said inflatable tubular support elements for inflating said inflatable tubular support elements with gas, said inflation means comprising a fan, said support elements supporting said plastic film elements in an inflated state in a region around said reclining surface to provide a deployed hood state;
a valve for preventing return of the gas upon inflating said tubular support elements with gas, the valve being operatively removable for allowing gas to escape from said tubular support elements for deflating said tubular support elements; and
a control unit connected to said fan and connected to said valve for controlling the valve and the fan to pump gas into said tubular support elements and to allow gas to escape from said tubular support elements for changing between said deployed hood state and a non-deployed hood state.

12. A thermotherapy device in accordance with claim 11, wherein said support elements are connected to one another such that said plastic film elements are tentered between said support elements in the inflated state to position one or more plastic film elements directly above said reclining surface or on sides of said reclining surface in the deployed hood state.

13. A thermotherapy device in accordance with claim 11, wherein said support elements are connected to one another such that said support elements have none of said plastic film elements in an area of one of shorter sides of said reclining surface in the inflated state, so that said one of shorter sides is open.

14. A thermotherapy device in accordance with claim 13, further comprising a wall for sealing and/or stabilizing a mounting of said hood on one of the shorter sides of the reclining surface.

15. A thermotherapy device in accordance with claim 11, wherein said plastic film consists of a plastic that is one of transparent and transparent to infrared radiation.

16. A thermotherapy device in accordance with claim 11, wherein said valve is a removable nonreturn and said control unit acts to operatively remove the removable nonreturn valve for changing between said deployed hood state and a non-deployed hood state wherein at least one of said support elements has the removable nonreturn valve for taking in air into one of said support elements or into all or a plurality of said support elements.

17. A thermotherapy device in accordance with claim 11, wherein at least one of said support elements includes a resetting element comprising an elastic cord.

18. A thermotherapy device in accordance with claim 11, wherein at least one of said support elements is provided with openings, perforations or pores and defines a conditioned warm and humid air conduit for conveying and for releasing conditioned air from an interior of said at least one of said support elements into an interior space defined by said hood and said reclining surface.

19. A thermotherapy device in accordance with claim 11, wherein said inflatable hood further comprises a separate side window with an inflatable window support element, said inflatable window support element being integrated in said inflatable hood.

20. A thermotherapy device in accordance with claim 11, wherein at least one of said plastic film elements has a double-walled design.

* * * * *